(12) United States Patent
Wicklund

(10) Patent No.: US 6,464,937 B2
(45) Date of Patent: Oct. 15, 2002

US006464937B2

(54) ULTRAPURE STERILIZATION OF MICROBIOLOGICAL TEST MEDIA BY ELECTRON BEAM IRRADIATION

(75) Inventor: Gary Wicklund, Boring, OR (US)

(73) Assignee: PML Microbiologicals, Inc., Wilsonville, OR (US)

(*) Notice: Subject to any disclaimer, the term of this patent is extended or adjusted under 35 U.S.C. 154(b) by 0 days.

(21) Appl. No.: 09/969,261

(22) Filed: Oct. 1, 2001

(65) Prior Publication Data

US 2002/0051729 A1 May 2, 2002

Related U.S. Application Data

(60) Provisional application No. 60/245,182, filed on Nov. 1, 2000.

(51) Int. Cl.[7] .................................................. A61L 2/08
(52) U.S. Cl. .......................................... 422/22; 53/425
(58) Field of Search ........................... 422/22; 206/204; 53/425

(56) References Cited

U.S. PATENT DOCUMENTS 4,657,133 A * 4/1987 Komatsu et al. ............ 206/204

FOREIGN PATENT DOCUMENTS

| JP | 10262646 | * 10/1998 |
| JP | 11319040 | * 11/1999 |

* cited by examiner

*Primary Examiner*—Robert J. Warden, Sr.
*Assistant Examiner*—Sean E. Conley
(74) *Attorney, Agent, or Firm*—Chernoff, Vilhauer, McClung & Stenzel, LLP

(57) ABSTRACT

Ultrasterile microbiological test media having a sterility assurance level of $10^{-6}$ is obtained by irradiation of the media by electron beams.

10 Claims, No Drawings

ULTRAPURE STERILIZATION OF MICROBIOLOGICAL TEST MEDIA BY ELECTRON BEAM IRRADIATION

The priority of Provisional Application Ser. No. 60/245,182 filed Nov. 1, 2000 is claimed.

BACKGROUND OF THE INVENTION

The field of industrial microbiology comprises the testing of environments, equipment and manufacturing facilities for sterility. The principal means by which such sterility testing is conducted is by obtaining an appropriate sample from the environment of concern and conducting a microbiological assay with the use of appropriate microbiological test media. The most basic problem encountered in the field of industrial microbiology is that of assuring that the test medium that is used will not itself contaminate the environment to be tested. Various degrees of sterility assurance level (SAL) are known. For example, in the United States the most commonly encountered SAL is $10^{-3}$, meaning that the level of contamination of vessels containing test media is $\leq 1$ in 1000 vessels that test positive for microbial contamination, while the international SAL is $10^{-6}$. For ultrasensitive sterility testing of clean rooms, surgical environments, pharmaceutical manufacturing environments and the like, an ultrapure test medium having an SAL of $10^{-6}$ is most desirable, yet difficult to achieve with standard methods.

Two common methods of achieving an SAL of $10^{-6}$ are by autoclaving and by irradiation with gamma rays. However, the drawback to autoclaving is that the outside of the container quickly becomes nonsterile following autoclaving upon exposure to a nonsterile environment. The drawback to gamma irradiation with respect to glass and plastic containers is that gamma rays cause clear glass to yellow and plastic to darken, making any growth in the media difficult to detect.

BRIEF SUMMARY OF THE INVENTION

The present invention overcomes these drawbacks of the prior art by imparting an SAL of $10^{-6}$ to test media that is relatively long lasting and that may be achieved simply and efficiently. The essence of the invention is the exposure of fluid test media in plastic containers to a beam of electrons.

DETAILED DESCRIPTION OF THE INVENTION

The generation of high energy electrons has recently become commercially available. High energy electrons are a form of ionizing radiation capable of killing microorganisms by creating highly reactive free radicals that break down the DNA of microorganisms, rendering them incapable of reproduction. At the same time, such ionizing radiation may attack the polymers of plastic vessels, causing depolymerization, grafting, crosslinking and chain scission and so care must be taken to select plastic vessels formed from polymers that are not susceptible to such unwanted chemical reactions. Known commercial sources of electron beam irradiation include Iotron Technologies, Inc. of British Columbia Canada and Titan Scan Systems of Denver, Colo. Iotron Technologies offers a 60 KWatt/10 MeV electron beam accelerator having a dosing range of from 0 to 100 kGy per pass.

According to the present invention, it has been discovered that test media having a typical bioburden on the order of $\leq 25$ colony-forming units (CFU) may be sterilized to an SAL of $10^{-6}$ by exposing the same to electron beam irradiation at a dosage of from about 15 kGy to about 30 kGy at a rate of from about 175 to about 225 cm/min., preferably 18 to 25 kGy at about 200 cm/min.

In an especially preferred embodiment, the test media vessels are bottles formed from cyclohexanedimethanol-modified polyethylene wherein the cap assembly of such a bottle is formed from polyethylene and polypropylene and the bottle optionally has a septum in the cap assembly formed from butyl rubber. Following irradiation by an electron beam no undesirable chemical reactions involving the polymer of the vessel and no undesirable darkening or yellowing is observed. A preferred arrangement of such sterility media-containing bottles for exposure to the electron beam irradition is 6 packs of 20 bottles each arranged uniformly on an exposure tray measuring approximately 40 inches×50 inches; each bottle has a 200 mL volume that is filled with approximately 100 mL fluid test media and each bottle is laid on its side so that the depth of the media is $\leq 1\frac{1}{2}$ inches. Average bioburden may be ascertained in accordance with the ANSI/AAMI/ISO 11137 protocol, Method 1, this bioburden number being ascertained prior to exposure of the media to the electron beam irradiation. The ANSI/AAMI/ISO 11137 Dose Audit protocol is preferably used for validation and periodic audits of the SAL.

EXAMPLE

One hundred and twenty 200 mL sterility testing bottles made of cyclohexanediol-modified polyethylene, each having a cap assembly made of polyethylene/polypropylene and a butyl rubber septum (commercially available as Duotek® bottles from PML Microbiologicals, Inc. of Wilsonville, Oreg.) and containing approximately 100 mL fluid microbiological test medium comprising an aqueous solution of tryptic soy broth were provided. Samples of the same test media were tested for average bioburden by the ANSI/AAMI/ISO 11137 protocol, Method 1 and the same was ascertained to be 22.4 colony-forming units (CFU). The 120 bottles containing test media were divided into 6 boxes with each box containing 4 sealed bags, the sealed bags in turn containing 5 bottles individually double-wrapped with a composite gas-impermeable film of polyvinylidene chloride over a polyester/polyethylene support, commercially available from LPS Industries of Moonachie, N.J. Each of the 6 boxes of 20 were placed in uniform spaced relationship on their sides on an exposure tray measuring approximately 40×50 inches, so that the depth of the fluid test medium was approximately $\leq 1\frac{1}{2}$ inches. The tray was exposed to electron beam irradiation in an IMPELA electron beam accelerator (10 MeV, 60 kwatt, 80 cm scan) from Iotron Technologies, Inc. of Port Coquitlam, B.C., Canada at a dosage of 16.5–24.4 kGy at a linear rate of 200 cm/min for an average of 15 seconds. This procedure was repeated on 141 additional 120-bottle batches. SAL on all 142 batches was calculated in accordance with the ANSI/AAMI/ISO 11137 Dose Audit protocol and the Stumbo equation used to calculate a D value factor:

$$D=RD/(\log A - \log B)$$

where

RD is radiation dose in kGy,

A is bioburden including extraction efficiency and $$B \text{ is } \frac{\text{samples tested}}{\text{sterile samples}}$$

and ascertained to be $10^{-6}$.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A method of sterilizing microbiological test media to a sterility assurance level of $10^{-6}$ comprising exposing said media to electron beam radiation at a dosage of from about 15 to about 30 kGy at a rate of from about 175 to about 225 cm/min.

2. The method of claim 1 wherein said dosage is from about 18 to 25 kGy and said rate is about 200 cm/min.

3. The product of the process of claim 1 or 2.

4. Sterile microbiological test medium contained in a vessel comprising microbiological test medium in a cyclohexanedimethanol-modified polyethylene vessel that has been exposed to electron beam radiation at a dosage of from about 15 to about 30 kGy at a rate of from about 175 to about 225 cm/min.

5. The test medium of claim 4 wherein said dosage is from about 18 to about 25 kGy and said rate is about 200 cm/min.

6. The test medium of claim 4 wherein said vessel further includes a polyethylene/polypropylene cap assembly.

7. The test medium of claim 6 wherein said vessel further includes a butyl rubber septum.

8. The test medium of claim 6 wherein said vessel is enclosed within a sealed package.

9. The test medium of claim 8 wherein said sealed package comprises a double gas-impermeable wrap.

10. The test medium of claim 9 wherein said gas-impermeable wrap comprises a composite film of polyvinylidene chloride/polyester/polyethylene.

* * * * *